United States Patent
Cavazza

(12) 
(10) Patent No.: US 6,306,392 B1
(45) Date of Patent: Oct. 23, 2001

(54) COMPOSITION COMPRISING A CARNITINE AND GLUTATHIONE, USEFUL TO INCREASE THE ABSORPTION OF GLUTATHIONE AND SYNERGIZE ITS EFFECTS

(75) Inventor: Claudio Cavazza, Rome (IT)

(73) Assignee: Sigma-Tau Healthscience S.p.A., Pomezia (IT)

( * ) Notice: Subject to any disclaimer, the term of this patent is extended or adjusted under 35 U.S.C. 154(b) by 0 days.

(21) Appl. No.: 09/719,176

(22) PCT Filed: Apr. 7, 2000

(86) PCT No.: PCT/IT00/00129

§ 371 Date: Dec. 15, 2000

§ 102(e) Date: Dec. 15, 2000

(87) PCT Pub. No.: WO00/62773

PCT Pub. Date: Oct. 26, 2000

(30) Foreign Application Priority Data

Apr. 16, 1999 (IT) ............................................. RM99A0230

(51) Int. Cl.[7] ........................ A01N 63/00; A61K 38/00; A61K 31/205; A61K 31/195

(52) U.S. Cl. ........................... 424/93.51; 514/2; 514/556; 514/561; 514/562

(58) Field of Search ................................. 514/2, 561, 562, 514/556; 424/93.51

(56) References Cited

FOREIGN PATENT DOCUMENTS

| 0 797 993 | * | 10/1997 | (EP) . |
| WO 97/34596 | * | 9/1997 | (WO) . |
| WO 98/4113 | * | 9/1998 | (WO) . |

* cited by examiner

*Primary Examiner*—Raymond Henley, III
(74) *Attorney, Agent, or Firm*—Oblon, Spivak, McClelland, Maier & Neustadt, P.C.

(57) ABSTRACT

A composition useful for increasing the absorption of glutathione and for synergizing its effects. This composition may take the form of a dietary supplement, dietetic support or of an actual medicine and comprises: (a) propionyl L-carnitine or a pharmacologically acceptable salt thereof; (b) glutathione or a glutathione-containing yeast; (c) a glutathione-free yeast if the component (b) consists of glutathione. The invention is also directed to methods of making this composition as well as to methods of prevention or treatment using it.

24 Claims, No Drawings

COMPOSITION COMPRISING A CARNITINE AND GLUTATHIONE, USEFUL TO INCREASE THE ABSORPTION OF GLUTATHIONE AND SYNERGIZE ITS EFFECTS

This is a 371 of PCT/IT00/00129 filed Apr. 17, 2000.

The present invention relates to a composition for the prevention and/or treatment of alterations of those organs which perform the most intense metabolic function, such as the liver, kidneys, cardiovascular system and brain.

More particularly, such composition is useful to treat or prevent hepatosis, nephropathies and cardiovascular or cerebral damages such as damages provoked by ageing or due to an altered metabolism of such organs or provoked by toxic substances.

Accordingly, the composition may take the form and exert the action of a dietary supplement or of an actual medicine, depending upon the support or preventive action, or the strictly therapeutic action, which the composition is intended to exert in relation to the particular individuals it is to be used in.

More particularly the present invention relates to an orally, parenterally, rectally, or transdermally administrable composition which comprises in combination:

(a) propionyl L-carnitine or a pharmacologically acceptable salt thereof, optionally in combination with another "carnitine", where for "carnitine" is intended L-carnitine or an alkanoyl L-carnitine selected from the group comprising acetyl L-carnitine, valeryl L-carnitine and isovaleryl L-carnitine or their pharmacologically acceptable salts; and (b) glutathione or glutathione-containing yeast;

(c) a glutathione-free yeast if the component (b) consists of glutathione.

Glutathione (GSH), N-(N-L-L-γ-glutamyl-cysteinyl) glycine, plays an essential role in the organic redox and detoxification reactions. Glutathione is synthesised in the body starting from glutamic acid and cysteine which, in the presence of ATP, form γ-glutamyl-cysteine, which, again in the presence of ATP, reacts with glycine giving rise to the formation of glutathione. Glutathione is ubiquitously present in the body. Its greatest concentrations, however, are to be found in the liver, heart and brain, i.e. in those organs where the metabolic, energy and detoxification reactions are more important. These tissues also contain glutathione peroxidase and glutathione reductase, which regulate the redox system related to the glutathione cycle, ensuring maintenance of sufficient amounts of reduced glutathione after the latter has been oxidised.

Though the biochemical and detoxifying activities of glutathione have long been known, particularly against heavy metals (which are among the most important environmental pollutants) or against liver-damaging drugs such as paracetamol, only the most recent researches have revealed the predominant role of glutathione among the various redox systems, as well as its specific pharmacological role. A direct involvement of glutathione in exerting a protective effect against the formation of atheromatous plaques has been observed by directly measuring the presence of the glutathione-related antioxidant/prooxidant system in such plaques. These researches revealed low concentrations of glutathione and fairly poor activity of the glutathione-related redox system. There was a particularly marked reduction in the glutathione peroxidase concentration and at the same time an increase in the concentration of oxidising factors. These abnormalities are not evident, however, in normal vascular tissue.

Glutathione also plays a major protective role in diseases of the liver. Moreover, the liver-protecting effects of many drugs are mediated by glutathione. It has also been reported that increased glutathione may reduce liver transplant rejection.

At the neurocerebral level, too, the role of glutathione distinguishes itself from that of the other better known redox systems in affording protection against the tissue and cell damage detected during ageing, in Parkinson's disease, or in Alzheimer's disease. At the cerebral level, in fact, glutathione is capable of playing various roles, and particularly that of a possible neurotransmitter. A deficiency of glutathione may increase the levels of cytotoxic substances and trigger the apoptosis of distinct sets of neuronal cells.

During ageing an increase in oxidative processes is observed and a reduction in natural antioxidant substances, including most notably glutathione, with the result that glutathione deficiency may be regarded as one of the causes of ageing. The favourable role of glutathione can also be observed at the intestinal level where its presence affects the formation of hydroperoxides and lipid peroxides, performing an important function of intestinal detoxification and in preventing the associated liver and bowel diseases.

L-carnitine and its alkanoyl derivatives are well known for the important role they may play at the metabolic level, particularly with regard to the oxidation and utilisation of fatty acids through β-oxidation.

L-carnitine, in fact, whether ingested with the diet or synthesised by the body, is concentrated by the blood in the organs which are metabolically most active in the utilisation of fatty acids, such as the skeletal muscles and heart.

An L-carnitine deficiency may be the cause of myopathy, whereas the oral administration of L-carnitine improves the clinical state associated with such diseases. L-carnitine also performs an important function in the mitochondrial oxidation of glucose in terms of energy production, with the result that adequate levels of L-carnitine are necessary for normal energy metabolism at the cardiac and muscular levels.

Its administration improves resistance to stress in subjects suffering from coronary insufficiency, as well as enhancing coronary flow, producing an improvement in the clinical effects of cardiac decompensation.

Other biological properties of L-carnitine and its alkanoyl derivatives, particularly of propionyl L-carnitine, are its ability to stabilise the cell membranes and protect them against the lesions induced by oxidative processes.

It has now surprisingly been found that a combination composition comprising as active ingredients:

(a) propionyl L-carnitine or one of its pharmacologically acceptable salts;

(b) glutathione or a glutathione-containing yeast;

(c) a glutathione-free yeast if the component (b) consists of glutathione; is extremely effective in the prevention and/or treatment of abnormalities of the metabolically most active organs such as the liver, kidneys, cardiovascular system and brain, both as a result of the potent synergistic effect exerted by its components and as a result of their increased tissue uptake, particularly of glutathione. Such a composition is particularly useful for the prevention or treatment of liver disease, kidney disease and cardiovascular or cerebral damage, such as, for instance, that produced by ageing, whether due to impaired metabolism of the above-mentioned organs or to toxic substances.

It has also been found that, advantageously, component (a) may further comprise another "carnitine", selected from the group comprising acetyl L-carnitine, valeryl L-carnitine and isovaleryl L-carnitine, or their pharmacologically acceptable salts or mixture thereof.

When component (a) of the composition consists of a mixture of carnitines, a mixture of L-carnitine, acetyl L-carnitine and propionyl L-carnitine or the pharmacologically acceptable salts thereof, is preferred.

When component (b) consists of glutathione, component (c) will then consist of a glutathione-free yeast, selected from the group comprising *Saccharomyces cerevisiae* and *Saccharomyces fragilis*. Other examples of such yeasts are well known to experts in the field.

When component (b) consists of a glutathione-containing yeast, the yeast should preferably contain from 7 to 10% of glutathione by weight. A non-limiting example of a suitable glutathione-containing yeast is the YH—Torula Yeast extract (*Candida utilis*) produced by Kohjin, Japan.

The (a):(b):(c) weight-to-weight ratio ranges from 100:1:100 to 1:10:10 and preferably from 10:1:10 to 1:1:1.

It has also been proved that both the synergistic effect and the tissue uptake are further increased when the composition also contains:

(d) at least one of the precursors of the biosynthesis of glutathione, selected from the group consisting of glutamic acid, glycine, cysteine and magnesium.

The optimal result is obtained when all the aforementioned precursors are present in the composition.

The preferred (a):(d) ratio is from 1:1 to 1:0.5.

The components constituting the combination according to the invention present an unexpected and surprising synergistic effect in protecting the body against toxic damages both of endogenous origin, such as metabolic damage due to ageing, and of exogenous origin, such as damage caused by environmental pollutants or by other damaging agents. In particular, the new composition may be usefully employed in the prevention and treatment of all those abnormalities which occur in association with ageing, whether of neurocerebral or cardiovascular origin, or in situations of parenchymal distress of organs, such as, for instance, the liver, which as a result of their metabolic and detoxifying action are more exposed to lesions induced by external toxic agents or by toxic metabolites.

The efficacy of the new composition stems both from the above-mentioned synergistic effect and from the increased active tissue concentrations of its components, particularly glutathione, as a result of their enhanced uptake.

The composition according to the invention can be used both as a food supplement or dietary supplement with a prevalently preventive action and as a drug for the treatment of frank disease conditions. The metabolic effects exerted both by carnitines or glutathione or the glutathione-containing yeast and by the amino acids present in the composition are well known, and a deficiency of such compounds in the body may cause diseases even of a serious nature. It was not, however, predictable that their combination could powerfully enhance the effects and favour processes of uptake, thus increasing their tissue concentrations. In particular, various forms of liver and brain distress, atherosclerotic abnormalities and intoxication due to heavy metals, chemotherapy agents or other drugs may benefit from the use of this composition.

The surprising synergistic effect produced by the combination of "carnitines" and glutathione in the presence of yeast and glutathione amino acid precursors and their enhanced uptake have been demonstrated in various pharmacological tests (some of which are described here below) selected because of their ability to provide highly predictive indications regarding the practical use of this composition both in the preventive/nutritional field and in the strictly therapeutic field.

Toxicology Tests

Prior to the various pharmacological tests the toxicity and tolerability limits of the new composition were tested in animals.

These toxicity tests were conducted both in rats and in mice, administering the various different products in combination in a single high-dose administration or administering them to the same animals continuously for at least sixty days. It was thus observed that one can administer an oral combination of up to 1 g/kg of propionyl L-carnitine and acetyl L-carnitine together with 500 mg/kg of glutathione or 2 g/kg of yeast containing 10% glutathione and also the same products together with glutamic acid (100 mg/kg), glycine (100 mg/kg), cysteine (100 mg/kg) and magnesium (10 mg/kg) without the appearance of any sign of intolerance or toxicity. Also well tolerated is the prolonged administration for sixty days of 0.5 g/kg of propionyl L-carnitine or acetyl L-carnitine together with 100 mg/kg of glutathione or with 1 g/kg of yeast extract containing 10% glutathione also together with glutamic acid (50 mg/kg), glycine (50 mg/kg) and magnesium (5 mg/kg).

Following these tests, examination of blood samples revealed no abnormalities of any kind in the animals treated. At autopsy, too, the histological tests performed on the main organs detected no changes of a pathological nature as compared to control animals.

Pharmacological Tests

To assess the antitoxic and anti-ageing liver-protective effects of the new composition various tests were selected from those which were not only better suited for revealing the pharmacological effects, but which were also reliably predictive for the purposes of its practical applications both as a nutritional and a pharmaceutical composition in the field of the prevention and treatment of liver diseases of toxic or metabolic origin and in diseases due to ageing.

Acetaminophen (Paracetamol) Induced Toxicity Tests

Various groups of male mice received oral administrations of 600 mg/kg acetaminophen, which is a dose sufficient to cause death within 24 hours in 50% of the animals thus treated.

At the same time as the acetaminophen administration, one group of animals (group G) were administered glutathione (G) and a second (group YG) were administered yeast containing 10% glutathione (YG); a third group (group PC) were administered propionyl L-carnitine (PC); a fourth group (group AA) were administered a combination of glutamic acid, cysteine, glycine and magnesium (AA); a fifth group (group CC) were administered a first combination according to the invention, called the "complete combination" (CC), consisting of PC+G+AA, while a sixth group (group CYC) were administered a second combination according to the invention, called the "complete yeast combination" (CYC), consisting of PC+YG+AA.

The mortality 24 hours after treatment was observed in all the groups treated. The results of the test are given in Table 1.

The results of these tests indicate that, whereas partial protection against the mortality induced by acetaminophen is achieved with glutathione, no such protection is observed after propionyl L-carnitine or with the amino-acid combination. Glutathione-containing yeast shows a greater degree of protective activity than that afforded by glutathione alone. When the complete yeast combination, CYC, is administered, the protection appears to be total, thus demonstrating an evident synergism between glutathione, propionyl L-carnitine and the other components of the combination.

These synergistic effects appear even more marked when the mice are administered a 900 mg/kg acetaminophen dose, which causes the deaths of 100% of the animals. In this case, only administration of the complete yeast combination, CYC, protects more than 50% of the animals treated against death (see Table 2).

The protection against acetaminophen at the dose of 900 mg/kg afforded by the new composition was even more marked when the animals were treated for 7 consecutive days prior to acetaminophen administration with the various components of the combination (see Table 3).

This result is probably related to the increased concentration of glutathione and the other components due to the greater tissue uptake related to the presence of yeast as well as to the increased synthesis of glutathione itself due to the greater presence of its precursors.

TABLE 1

Protection against acetaminophen-induced mortality (600 m/kg/%).

| Treatment/animal groups | mg/kg | Mortality |
|---|---|---|
| C | — | 6/10 |
| PC | 100 | 6/10 |
| G | 50 | 4/10 |
| YG | 500 | 3/10 |
| AA | 130 | 5/10 |
| CC | 280 | 2/10 |
| CYC | 780 | 0/10 |

C = Controls
PC = Propionyl L-carnitine
G = Glutathione
YG = Yeast containing 10% glutathione
AA = Combination of amino acids and magnesium (glutamic acid 30 mg, cysteine 25 mg, glycine 50 mg + magnesium 5 mg)
CC = Complete combination = (PC + G + AA)
CYC = Complete yeast combination = (PC + YG + AA)

TABLE 2

Protection against acetaminpohen-induced mortality (900 mg/kg/%).

| Treatment/animal groups | mg/kg | Mortality |
|---|---|---|
| C | — | 10/10 |
| PC | 100 | 10/10 |
| G | 50 | 7/10 |
| YG | 500 | 6/10 |
| AA | 130 | 9/10 |
| CC | 280 | 5/10 |
| CYC | 780 | 3/10 |

TABLE 3

Protection against acetaminophen-induced mortality (900 mg/kg/%) after prolonged prior administration of the composition or its components for 7 conservative days.

| Treatment | mg/kg | Mortality |
|---|---|---|
| C | — | 10/10 |
| PC | 100 | 9/10 |
| G | 50 | 5/10 |
| YG | 500 | 3/10 |
| AA | 130 | 9/10 |
| CC | 280 | 1/10 |
| CYC | 780 | 0/10 |

Carbon Tetrachloride ($CCl_4$) Intoxication Tests on Isolated Rat Liver Cells

In addition to intoxication with acetaminophen, the protective and synergistic activity exerted by the various components of the composition according to the invention are also detected at the hepatic level in relation to $CCl_4$ intoxication. The cells used in these tests were isolated rat liver cells after perfusion with collagenase according to the method described by Seglen (Seglen F. O., *Method Cell. Biol. Chem.* 264:4747, 1989). Approximately $4-6 \times 10^8$ viable liver cells were collected, calculated by exclusion of non-viable cells by means of trypan blue.

The cells thus isolated were suspended in 25 $cm^2$ plastic receptacles in the presence of antibiotics and 10% inactivated fetal calf serum. To the cell suspension thus obtained was added $CCl_4$ (10 mmol.$L^{-1}$), glutathione (GSH 20 mg.$L^-$1), propionyl L-carnitine (100 mg.$L^{-1}$) or glutathione combined with propionyl L-carnitine. After a 4-h incubation the percentage of dead cells was estimated by release of lactate dehydrogenase, as described by Casini et al. (Casini et al., *J. Biol. Chem.*, 257:6721, 1982). The examination of the protective effect against $CCl_4$ intoxication exerted by glutathione, propionyl L-carnitine and their use in combination was determined by assay of culture supernatant for both alanine aminotransferase (Ala AT) and aspartate aminotransferase (Asp AT) (Auto-biochemistry Assay System Beckman 700-Encore 2).

The cytological examination of the liver cells was done under both the light and electron microscope after fixation in 3% formalin and paraffin for light microscopy and 3% glutaraldehyde and 1% osmium tetroxide for electron microscopy.

The results of this analysis (see Tables 4, 5 and 6) demonstrate that both glutathione and propionyl L-carnitine are capable of reducing the toxic effects of carbon tetrachloride.

Surprisingly, higher effect was obtained from the combination of glutathione together with PLC.

In this case, the percentage of dead cells was reduced practically to zero. The increase in enzyme concentrations indicative of metabolic functional damage (Ala AT–Asp AT) was also unexpectedly substantially reduced by the combination of glutathione and propionyl L-carnitine. Confirmation of the intense synergistic effect of glutathione and propionyl L-carnitine was also provided by the histological examinations which, at light microscopy, revealed the virtually complete disappearance of necrotic cells and, at electron microscopy, showed preservation of the intracellular structures and, in particular, of the mitochondrial structures and the number of ribosomes.

TABLE 4

Protection in CCl$_4$-intoxicated liver cell cultures

| Treatment | % dead cells |
|---|---|
| CCl$_4$ | 85 ± 4 |
| Glutathione | 55 ± 5 |
| Propionyl L-carnitine | 70 ± 7 |
| Glutathione + Propionyl L-carnitine | 5 ± 3 |

TABLE 5

Protection in CCl$_4$-intoxicated liver cell cultures. Concentrations of alanine aminotransferase (Ala AT nmol.min$^{-1}$ L$^{-1}$) and of aspartate aminotransferase (Asp AT nmol.min$^{-1}$.L$^{-1}$) in supernatant after 4 hours

| Treatment | Ala AT | Asp AT |
|---|---|---|
| CCl$_4$ | 26.5 ± 3.1 | 9.08 ± 0.7 |
| Glutathione | 19.7 ± 2.5 | 7.5 ± 5.4 |
| Propionyl L-carnitine | 22.4 ± 2.8 | 8.9 ± 0.9 |
| Glutathione + Propionyl L-carnitine | 7.7 ± 1.9 | 3.4 ± 2.1 |

Carbon Tetrachloride-induced Liver Intoxication Tests

Another indicator of CCl$_4$ toxicity in the liver is provided by the increased hepatic concentration of triglycerides. In this test, too, the protective activity of glutathione, propionyl L-carnitine, amino acids and yeast, both alone and in combination in the composition according to the invention, was demonstrated.

The CCl$_4$ intoxication was induced by giving fasting rats an intraperitoneal injection of 1 ml.kg$^{-1}$ of a suspension of 20% CCl$_4$ in olive oil. Prior to CCl$_4$ intoxication the rats were treated for three consecutive days with glutathione (G=50 mg/kg), or with propionyl L-carnitine (PC=100 mg/kg), or with yeast containing 10% glutathione (YG=500 mg/kg), or with a combination of amino acids (AA=glutamic acid 50 mg, cysteine 25 mg, glycine 50 mg, magnesium 5 mg). or with the complete combination CC (CC=PC+G+ AA), or with the complete yeast combination CYC (CYC= PC+YG+AA). After administration of CCl$_4$, the livers were excised from the decapitated animals and were used to measure the triglyceride concentration according to the method described by Donabedian (Donabedian R. K., *Clin. Chem.*, 20:632, 1974). The results of these tests also revealed a substantial synergism between glutathione and propionyl L-carnitine in protecting the liver against CCl$_4$ intoxication.

Even more marked was the protective effect of the combination of propionyl L-carnitine with yeast and the amino acid complex. In this case, in fact, liver infiltration by triglycerides was practically non-existent, thus demonstrating the powerful synergism achieved by the composition according to the invention (see Table 6).

TABLE 6

Tests on increase in liver triglycerides induced by CCl$_4$

| CCl$_4$ (ml.kg$^{-1}$) | Treatments | Triglycerides (mg.g$^{-1}$) |
|---|---|---|
| 0 | — | 5.9 ± 0.4 |
| 1 | — | 26.9 ± 1.1 |
| 1 | PC | 20.2 ± 1.9 |
| 1 | G | 18.7 ± 2.1 |
| 1 | YG | 16.5 ± 1.2 |
| 1 | AA | 20.4 ± 2.1 |
| 1 | CC | 12.5 ± 1.4 |
| 1 | CYC | 9.9 ± 0.6 |

Protection Against Experimental Hypertriglyceridaemia in the Rat

The method used for this test was that described by Carlson (Carlson L. A. V., *J. Atheroscl. Res.*, 8:667, 1968) and modified as described in *Atherosclerosis*, 16:349, 1972. According to this test oral administration of 3 g/kg of fructose in the rat induces a substantial increase in both liver and serum triglycerides five hours after administration.

The aim of this test was to assess whether the administration of the components of the composition according to the invention, when used alone or in combination, were capable of leading to a reduction in this triglyceride abnormality which is regarded as underlying severe liver dysfunctions as well as atherosclerosis.

To this end, various groups of rats were treated with glutathione (G=50 mg/kg), with propionyl L-carnitine (PC= 50 mg/kg), or with yeast containing 10% glutathione (YG= 500 mg/kg), or with an amino acid mixture (AA=glutamic acid 50 mg/kg, cysteine 25 mg/kg, glycine 100 mg/kg+ magnesium 5 mg/kg), or with a combination of these various components (at the same doses) without yeast (CC) or with yeast (CYC). The treatment was given orally on the three days preceding fructose administration and for three hours after its administration. Five hours after fructose administration all animals were sacrificed and blood samples were used to assay triglycerides according to the method described by Donabedian (Donabedian R. K., *Clin. Chem.*, 20:632, 1974). The results of these tests indicate that both glutathione and propionyl L-carnitine have small efficacy on serum triglyceride levels induced by the administration of fructose, but that a marked effect is obtained when these compounds are given in combination, particularly in the presence of yeast. A substantial reduction in triglycerides was, in fact, observed in the blood of rats who had been administered the complete combination together with yeast and amino acids, thus demonstrating the powerful synergism between the various components of the combination (see Table 7).

TABLE 7

Tests on hypertriglyceridaemia (mg/100 ml) induced in the rat

| Controls | 190 ± 6.7 |
|---|---|
| G | 180 ± 5.9 |
| YG | 175 ± 6.9 |
| PC | 185 ± 7.1 |
| YG + PC | 155 ± 8.1 |
| AA | 185 ± 6.5 |
| CC | 140 ± 4.3 |
| CYC | 133 ± 6.3 |

Experimental Atherosclerosis Tests

The method used in this test was that described by Malinow (Malinow M. R., *Atherosclerosis*, 48:105, 1983).

According to this test, the administration for six weeks consecutively to male Wistar rats of an atherogenic diet consisting of 10% cotton oil, 24% casein, 1% cholesterol, 60% sugar, and vit. $D_2$ 200 mUST/g diet induces pronounced vascular atherosclerotic lesions. These are determined at the level of the aorta by measuring the thickness of the abdominal aorta using a morphometric method and the intensity of the staining induced by Sudan IV and by evaluating their severity with a scoring system from 1 to 5.

The morphometric assessments and the intensity of the Sudan IV staining again revealed, in these tests, too, a substantial synergism between glutathione (25 mg/kg) and propionyl L-carnitine (100 mg/kg), but the protective effect was even more marked when the complete yeast combination was used. In the group of rats treated with CYC the occurrence of vascular atherosclerotic lesions appeared, in fact, to be completely inhibited, demonstrating in this case, too, the synergistic activity of the various components of the combination according to the invention.

Activity Against Glycerol-induced Nephropathy

The method used in this test was that described by Young (Young J. H. K., *Meth. Find. Exp. Clin. Pharmacol.,* 13:23, 1991). According to this test, a glycerol injection induces kidney failure and nephropathy in the rat. This method was used to assess the protective effects of the combination according to the invention on the kidney. Male Sprague-Dawley rats were used, which, after being deprived of drinking water for 24 hours, were injected with 10 cc/kg of a 50% w/v solution of glycerol and water. After the injection, the animals thus treated were allowed to drink. After 24 hours, blood samples were taken from the animals and, after centrifuging, the plasma creatinine concentration was assayed (according to the method described by Taussky H. H., *Clin. Chem. Acta,* 1:210, 1956) and urea by means of reaction with diacetylmonoxime (Henry R. Y., Cannon D. C. Eds., *Clinical Chemistry,* 2 Ed. Harper & Rowe, London 1974). Propionyl L-carnitine (100 mg/kg), glutathione (50 mg/kg) or yeast containing glutathione (500 mg/kg), amino acids (25 mg/kg each), yeast (500 mg/kg) and a combination of these at the same doses were administered daily on the three days preceding the test. The results of this test (see Table 8) indicate that both propionyl L-carnitine and glutathione have a fairly good protective effect against glycerol-induced kidney lesions, but greater efficacy is obtained by their combined use, particularly in the presence of yeast. With the presence of amino acids, in addition to yeast, the protection afforded is practically total, thus demonstrating the effective potentiation of activity obtained with the combination and not only the synergism which exists between proprionyl L-carnitine and glutathione but also the favourable action exerted by yeast and amino acids on this combination.

TABLE 8

Protective activity against glycerol-induced kidney failure in the rat

| Treatment | Creatinine (mg/ml) | Urea (mg/100 ml) |
|---|---|---|
| Controls | 56.8 ± 7.7 | 22.2 ± 1.9 |
| Glycerol | 360.4 ± 55.2 | 116.7 ± 19.4 |
| Propionyl L-carnitine | 280.5 ± 22.5 | 88.5 ± 11.5 |
| Glutathione | 240.8 ± 20.9 | 79.9 ± 9.9 |
| Propionyl L-carnitine + Glutathione | 185.5 ± 19.2 | 60.2 ± 6.5 |
| Propionyl L-carnitine + Yeast (10% glutathione) | 160.8 ± 16.8 | 52.5 ± 6.1 |
| Amino acids | 320.4 ± 50.6 | 105.5 ± 14.9 |
| Propionyl L-carnitine + Glutathione + Amino acids + Yeast | 95.4 ± 9.2 | 38.4 ± 4.1 |

Effects on Glutathione (GSH) Concentration in Elderly Rats

Since the metabolic and enzymatic activity of glutathione is known to be reduced in elderly rats and this reduction is regarded as one of the causes of ageing, the effect of the administration of the new composition or its individual components on glutathione concentrations in the plasma and liver of young and elderly rats was evaluated.

For this test two different groups of rats were used: young rats (2–3 months) and elderly rats (8–10 months). The glutathione (GSH) concentration was calculated in both groups according to the technique described by Moron (Moron M. S., *Biochem. Biophys. Acta,* 582:67, 1979) both before the start of the test and after 15 days' daily administration of propionyl L-carnitine (100 mg/kg), glutathione (50 mg/kg), propionyl L-carnitine with glutathione or with yeast containing 10% glutathione (500 mg/kg), amino acids (500 mg/kg) or the combination according to the invention.

After 15 days of treatment, assay of the glutathione concentrations present in both the liver (see Table 9) and plasma (see Table 10) showed the reciprocal potentiation of propionyl L-carnitine and glutathione in restoring normal glutathione concentrations in elderly rats. The synergism, however, was even more marked in the presence of yeast and amino acids when mixed in the composition according to the invention.

TABLE 9

Effects on glutathione concentration (GSH ng/mg protein) in young and elderly rat livers

| | Young rats time | | Elderly rats time | |
|---|---|---|---|---|
| Treatment | 0 | 15 days | 0 | 15 days |
| Controls | 11.55 ± 0.88 | 12.75 ± 0.91 | 8.70 ± 0.72 | 8.10 ± 0.63 |
| Propionyl L-carnitine | 11.25 ± 0.41 | 12.90 ± 0.71 | 7.9 ± 0.51 | 9.3 ± 0.46 |
| Glutathione | 12.1 ± 0.36 | 12.85 ± 0.66 | 8.82 ± 0.69 | 9.90 ± 0.76 |

TABLE 9-continued

Effects on glutathione concentration (GSH ng/mg protein) in young and elderly rat livers

| Treatment | Young rats time | | Elderly rats time | |
|---|---|---|---|---|
| | 0 | 15 days | 0 | 15 days |
| Propionyl L-carnitine + Glutathione | 12.70 ± 0.64 | 13.05 ± 0.55 | 8.10 ± 0.71 | 10.50 ± 0.40 |
| Propionyl L-carnitine + Yeast (10% glutathione) | 11.73 ± 0.49 | 13.75 ± 0.62 | 8.75 ± 0.41 | 10.80 ± 0.71 |
| Amino acids | 11.25 ± 0.68 | 12.68 ± 0.41 | 8.90 ± 0.57 | 9.15 ± 0.68 |
| Propionyl L-carnitine + Glutathione + Amino Acids + Yeast | 11.35 ± 0.77 | 12.45 ± 0.59 | 8.25 ± 0.61 | 11.95 ± 0.85 |

TABLE 10

Effects on gluthathoine (GSH) concentration (GSH mg/dl) in young and elderly rat plasma

| Treatment | Young rats time | | Elderly rats time | |
|---|---|---|---|---|
| | 0 | 15 days | 0 | 15 days |
| Controls | 2.12 ± 0.59 | 2.25 ± 0.39 | 1.39 ± 0.49 | 1.35 ± 0.55 |
| Propionyl L-carnitine | 2.22 ± 0.29 | 2.39 ± 0.50 | 1.40 ± 0.22 | 1.75 ± 0.20 |
| Glutathione | 2.09 ± 0.31 | 2.35 ± 0.35 | 1.26 ± 0.31 | 1.80 ± 0.41 |
| Propionyl L-carnitine + Glutathione | 2.14 ± 0.21 | 2.40 ± 0.40 | 1.22 ± 0.21 | 1.95 ± 0.35 |
| Propionyl L-carnitine + Yeast (10% glutathione) | 2.20 ± 0.19 | 2.48 ± 0.33 | 1.35 ± 0.33 | 2.05 ± 0.29 |
| Amino acids | 2.27 ± 0.27 | 2.42 ± 0.29 | 1.33 ± 0.21 | 1.40 ± 0.34 |
| Propionyl L-carnitine + Glutathione + Amino Acids + Yeast | 2.10 ± 0.16 | 2.36 ± 0.26 | 1.25 ± 0.16 | 2.25 ± 0.39 |

Effects on Glutathione Uptake and Concentration in Blood of Glutathione-depleted Animals The aim of these tests was to demonstrate that the composition according to the invention favours the uptake of glutathione as a result of the presence of yeast.

To this end, the glutathione content in the blood of a group of Sprague-Dawley male rats was reduced by means of the administration of diethylmaleate (DEM)a depletor of glutathione, according to the technique described by Plummer (Plummer J., *Chemical depletion of glutathione "in vivo"*, Methods in Enzymology, 77:50, 1981). DEM was administered intraperitoneally to fasting rats at the dose of 1 cc/kg. Half an hour after injection of diethylmaleate, glutathione alone (50 mg/kg), or yeast containing 10% glutathione (500 mg/kg), or 50 mg/kg of glutathione together with 500 mg of yeast not containing glutathione were administered orally. Another group of rats received glutathione amino acid precursors (glutamic acid 50 mg/kg, glycine 50 mg/kg, cysteine 50 mg/kg, magnesium 10 mg/kg) or the complete combination according to the invention at the same doses as described here above.

After four hours blood samples were taken from the animals thus treated and the plasma glutathione concentration was measured. The results of these tests (see Table 11) indicate that glutathione uptake is substantially increased by the presence of yeast, whether the yeast contains glutathione or is simply used in combination with glutathione.

The presence of yeast caused a significant increase in glutathione plasma concentrations in rats in which these concentrations had been reduced by injection of DEM.

This effect was even more marked when the glutathione-depleted animals were administered the complete combination according to the invention.

TABLE 11

Effects on glutathione (GSH) concentration in plasma (GSH mg/dl) in glutathione-depleted rats by injecting diethylmaleate (DEM). Values measured 4 h after injection.

| | Glutathione (GSH mg/dl) |
|---|---|
| Controls | 2.70 ± 0.41 |
| DEM | 0.61 ± 0.74 |
| Propionyl L-carnitine | 0.70 ± 0.54 |
| Glutathione | 0.95 ± 0.88 |
| Yeast (10% glutathione) | 1.65 ± 0.90 |
| Glutathione + Yeast | 1.85 ± 0.80 |
| Amino acids | 0.85 ± 0.70 |
| Glutathione + Amino acids | 1.10 ± 0.66 |
| Propionyl L-carnitine + Glutathione + Amino acids + Yeast | 2.15 ± 1.1 |

Some non-limiting examples of composition according to the invention are reported hereinbelow.

| | |
|---|---|
| 1) Carnitine mixture | 200 mg |
| (L-carnitine 50 mg, acetyl L-carnitine 50 mg, propionyl L-carnitine 50 mg, isovaleryl L-carnitine 50 mg) | |
| Yeast (titled 7–10% glutathione) | 200 mg |
| Glutamic acid | 50 mg |
| L-cysteine | 50 mg |
| Glycine | 50 mg |
| Magnesium citrate | 10 mg |
| 2) Carnitine mixture | 200 mg |
| (L-carnitine 50 mg, acetyl L-carnitine 50 mg, propionyl L-carnitine 50 mg, isovaleryl L-carnitine 50 mg) | |
| Glutathione (GHS) | 50 mg |
| Glutamic acid | 50 mg |
| L-cysteine | 50 mg |

-continued

|   |   |   |
|---|---|---|
| Glycine | 50 | mg |
| Magnesium citrate | 10 | mg |
| Yeast (Saccharomyces cerevisias) | 200 | mg |
| 3) Propionyl L-carnitine | 200 | mg |
| Yeast (titled 7–10% glutathione) | 200 | mg |
| Glutamic acid | 50 | mg |
| L-cysteine | 50 | mg |
| Glycine | 50 | mg |
| Magnesium citrate | 10 | mg |
| 4) Propionyl L-carnitine | 200 | mg |
| Glutathione (GHS) | 50 | mg |
| Glutamic acid | 50 | mg |
| L-cysteine | 50 | mg |
| Glycine | 50 | mg |
| Magnesium citrate | 10 | mg |
| Yeast (Saccharomyces cerevisias) | 200 | mg |
| 5) Propionyl L-carnitine | 200 | mg |
| Glutathione | 100 | mg |
| Glutamic acid | 50 | mg |
| L-cysteine | 50 | mg |
| Glycine | 50 | mg |
| Magnesium citrate | 10 | mg |
| Yeast (Saccharomyces cerevisias) | 200 | mg |
| 6) Propionyl L-carnitine | 200 | mg |
| Yeast (titled 7–10% glutathione) | 300 | mg |
| Glutamic acid | 50 | mg |
| L-cysteine | 50 | mg |
| Glycine | 50 | mg |
| Magnesium citrate | 10 | mg |
| 7) Propionyl L-carnitine | 200 | mg |
| Glutathione (GSH) | 100 | mg |
| Glutamic acid | 50 | mg |
| L-cysteine | 50 | mg |
| Glycine | 50 | mg |
| Magnesium citrate | 10 | mg |
| β-carotene | 5 | mg |
| α-carotene | 5 | mg |
| Coenzyme Q10 | 10 | mg |
| Selenium methionine | 20 | μg |
| Yeast (Saccharomyces cerevisias) | 200 | mg |
| 8) Propionyl L-carnitine | 200 | mg |
| Yeast (titled 7–10% glutathione) | 300 | mg |
| Glutamic acid | 50 | mg |
| L-cysteine | 50 | mg |
| Glycine | 50 | mg |
| Magnesium citrate | 10 | mg |
| β-carotene | 5 | mg |
| α-carotene | 5 | mg |
| Coenzyme Q10 | 10 | mg |
| Vit. PP | 25 | mg |
| Vit. $B_6$ | 25 | mg |
| Vit. $B_{12}$ | 250 | μg |
| Selenium methionine | 20 | μg |

What is meant by pharmacologically acceptable salt of L-carnitine or alkanoyl L-carnitine is any salt of these active ingredients with an acid that does not give rise to unwanted toxic or side effects. These acids are well known to pharmacy experts.

Non-limiting examples of suitable salts are the following: chloride; bromide; iodide; aspartate, acid aspartate; citrate, acid citrate; tartrate; phosphate, acid phosphate; fumarate; acid fumarate; glycerophosphate; glucose phosphate; lactate; maleate, acid maleate; orotate; oxalate, acid oxalate; sulphate, acid sulphate, trichloroacetate, trifluoroacetate and methanesulphonate.

A list of FDA-approved pharmacologically acceptable salts is given in *Int. J. of Pharm.* 33, (1986), 201–217; this latter publication is incorporated herein by reference.

The compositon according to the invention may also comprise vitamins, coenzymes, minerals substances and antioxidants.

Appropriate excipients to be used to prepare the compositions having regards to the specific route of administration, will be apparent to the pharmacy and food industry experts.

What is claimed is:

1. A composition that comprises:
    (a) propionyl L-carnitine or a pharmacologically acceptable salt thereof; and
    (b) glutathione or a glutathione-containing yeast;
    (c) a glutathione-free yeast if the component (b) consists of glutathione.

2. The composition of claim 1, further comprising L-carnitine, acetyl L-carnitine, valeryl L-carnitine, isovaleryl L-carnitine or a pharmacologically acceptable salt thereof or a mixture thereof.

3. The composition of claim 2, that comprises a mixture of L-carnitine, acetyl L-carnitine and propionyl L-carnitine or their pharmacologically acceptable salts.

4. The composition of claim 1, wherein the glutathione-containing yeast contains from 7 to 10% by weight of glutathione.

5. The composition of claim 1, wherein the weight ratio (a):(b):(c) is from 100:1:100 to 1:10:10.

6. The composition of claim 1, further comprising:
    (d) at least one of the precursors of the biosynthesis of glutathione, selected from the group comprising glutamic acid, cysteine and magnesium.

7. The composition of claim 6, wherein the weight ratio (a):(d) is from 1:1 to 1:0.5.

8. The composition of claim 1, that comprises:
    (a) propionyl L-carnitine or a pharmacologically acceptable salt thereof;
    (b) glutathione;
    (c) a glutathione-free yeast, selected from the group comprising *Saccharomyces cerevisiae* and *Saccharomyces fragilis*;
    (d) glutamic acid, glycine, cysteine and magnesium.

9. The composition of claim 1, that comprises:
    (a) propionyl L-camitine or a pharmacologically acceptable salt thereof;
    (b) a yeast containing 7–10% by weight of glutathione;
    (c) glutamic acid, glycine, cysteine and magnesium.

10. The composition of claim 1, that comprises:
    (a) a mixture of L-carnitine, acetyl L-carnitine, propionyl L-carnitine or their pharmacologically acceptable salts;
    (b) glutathione;
    (c) a glutathione-free yeast, selected from the group comprising *Saccharomyces cerevisiae* and *Saccharomyces fragilis*;
    (d) glutamic acid, glycine, cysteine and magnesium.

11. The composition of claim 1, that comprises:
    (a) a mixture of L-carnitine, acetyl L-carnitine, propionyl L-carnitine or their pharmacologically acceptable salts thereof;
    (b) a yeast containing 7–10% by weight of glutathione;
    (c) glutamic acid, glycine, cysteine and magnesium.

12. The composition of claim 1 wherein the pharmacologically acceptable salt of L-carnitine or alkanoyl L-carnitine is selected from the group comprising: chloride; bromide; iodide; aspartate, acid aspartate; citrate, acid citrate; tartrate; phosphate, acid phosphate; fumarate, acid fumarate; glycerophosphate; glucose phosphate; lactate; maleate, acid maleate; orotate; acid oxalate; sulphate, acid sulphate; trichloroacetate; trifluoroacetate and methane sulphonate.

13. The composition of claim 1, that further comprises a vitamin, coenzyme, mineral substance or antioxidant.

14. The composition of claim 1, orally administrable, in the form of a dietary supplement.

15. The composition of claim 1 in the form of a medicament that is orally, parenterally, rectally or transdermally administrable.

16. The dietary supplement of claim 14, in a dosage effective for the prevention of hepatosis, nephropathies and cardiovascular or cerebral damages due to an altered metabolism of the corresponding organs or provoked by toxic substances.

17. The medicament of claim 15, in a dosage effective for the therapeutic treatment of hepatosis, nephropathies and cardiovascular or cerebral damages due to an altered metabolism of the corresponding organs or provoked by toxic substances.

18. The dietary supplement of claim 16, in the form of a tablet, lozenge, pill, capsule, granulate or syrup.

19. The medicament of claim 17, in the form of a tablet, lozenge, pill, capsule, granulate, syrup, suppository, vial or drop.

20. A method for preparing a dietary supplement or a medicament comprising admixing
   (a) propionyl L-carnitine or a pharmacologically acceptable salt thereof;
   (b) glutathione or a glutathione-containing, yeast;
   (c) a glutathione-free yeast if the component (b) consists of glutathione.

21. The method of claim 20 further comprising admixing:
   (d) at least one precursor of the biosynthesis of glutathione selected from the group consisting of glutamic acid, glycine, cysteine and magnesium.

22. A method for preventing or treating hepatosis, nephropathy, cardiovascular damage, or cerebral damage comprising administering an effective dose of the composition of claim 1 to a subject in need thereof.

23. The composition of claim 1, wherein the weight ratio (a):(b):(c) is from 10:1:10 to 1:1:1.

24. A method for reducing the toxicity of, or for detoxifying a toxic compound, comprising administering an effective dosage of the composition of claim 1 to subject in need thereof.

* * * * *